United States Patent [19]

Shea

[11] 3,950,538

[45] Apr. 13, 1976

[54] ANTI-INFLAMMATORY METHODS UTILIZING CERTAIN THIOUREAS

[75] Inventor: Philip J. Shea, Midland, Mich.

[73] Assignee: The Dow Chemical Company, Midland, Mich.

[22] Filed: Nov. 7, 1974

[21] Appl. No.: 521,614

Related U.S. Application Data

[63] Continuation of Ser. No. 452,032, March 18, 1974, abandoned.

[52] U.S. Cl. .................................................. 424/322
[51] Int. Cl.² ......................................... A61K 31/17
[58] Field of Search .................................... 424/322

[56] References Cited
UNITED STATES PATENTS
3,767,816   10/1973   Moss et al. ........................... 424/322

Primary Examiner—Stanley J. Friedman
Attorney, Agent, or Firm—Maynard R. Johnson

[57] ABSTRACT

A method of alleviating symptoms of inflammation in a mammal suffering from an inflammatory condition which comprises the administration to such mammal of a pharmaceutically effective amount of a 1-aryl-3-(2-hydroxyethyl)thiourea derivative.

26 Claims, No Drawings

ANTI-INFLAMMATORY METHODS UTILIZING CERTAIN THIOUREAS

CROSS REFERENCE TO RELATED APPLICATION

This is a continuation of application Ser. No. 452,032, filed Mar. 18, 1974, now abandoned.

BACKGROUND OF THE INVENTION

The present invention relates to the pharmaceutical field and more particularly to methods for treating inflammation in mammals utilizing as active agents certain 1-aryl-3-(2-hydroxyethyl)-thiourea derivatives.

The preparation of various 1-aryl-3-(2-hydroxyethyl)thioureas is disclosed in the art. Typically, such compounds are commonly prepared by the addition of ethanolamine to an aryl isothiocyanate. For example, the preparation of 1-(2,4-dimethylphenyl)-3-(2-hydroxy-ethyl)thiourea and related compounds is disclosed in U.S. Pat. No. 3,767,816. Compounds wherein the aryl moiety bears a methoxy substituent are similarly prepared by employing a corresponding methoxy substituted aryl isothiocyanate reactant. The above patent reference teaches the use of such compounds as diuretic agents. French Pat. No. 1,356,908 also discloses such structures only as intermediates for the preparation of 2-(arylamino)thiazolines. Schroeder, in *Chem. Reviews* 55, 183-189 (1955), discusses the biological properties of many thiourea compounds. Specific properties discussed include antitubercular, antithyroid, hypnotic, anesthetic, anthelmintic, antibacterial, antiphenoloxidase, insecticidal and rodenticidal properties. Anti-inflammatory properties are not discussed.

SUMMARY OF THE INVENTION

The essential feature of this discovery is the anti-inflammatory utility of a class of thioureas of the generic formula:

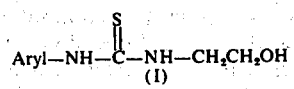

(I)

wherein aryl represents 2,4-dimethylphenyl, 4-methylphenyl, 3,5-dimethylphenyl, 2-methylphenyl, 2,4,6-trimethylphenyl, 3,4-dimethylphenyl, 2,6-dimethylphenyl, 3-methylphenyl, 2,5-dimethylphenyl, 2,4-dimethylbenzyl, 3,4-dimethoxyphenyl, 4-methoxy-2-methylphenyl, 6-methoxy-3-methylphenyl, 2-fluorophenyl, 3-fluorophenyl, 2,6-difluorophenyl, 2,5-difluorophenyl, 4-chlorophenyl, 2,4-dichlorophenyl, 2-chlorophenyl, 2,4,6-trichlorophenyl, 3-chloro-2-methoxyphenyl, 5-chloro-6-methoxyphenyl, 2-chloro-5-methoxyphenyl and 3-chloro-4-fluorophenyl. The foregoing compounds are, for convenience, hereinafter referred to as "thioureas".

DESCRIPTION OF THE PREFERRED EMBODIMENTS

The thiourea compounds employed as anti-inflammatory agents in the methods of the present invention are administered internally, i.e., orally or parenterally. Such compounds can be formulated into various pharmaceutical dosage forms such as tablets, capsules, solutions, suspensions, pills and the like, for immediate or sustained release, by combining the active compounds with suitable pharmaceutically acceptable carriers or diluents according to methods well known in the art. Such dosage forms may additionally include excipients, binders, fillers, flavoring and sweetening agents and other therapeutically inert ingredients necessary in the formulation of the desired pharmaceutical preparation. Various diluents, dosage forms, and other variations and modifications are well within the ability of those skilled in the art. Such ramifications are deemed to be within the scope of this invention.

Preferred thioureas employed in the methods of the present invention include those wherein aryl is selected from the group consisting of 2,4-dimethylphenyl, 2-methylphenyl, 2,4-dimethylbenzyl, 3,5-dimethylphenyl 4-methylphenyl and 2,4,6-trimethylphenyl. Another preferred class of compounds employed in the methods of the present invention include those wherein aryl represents 3-chloro-2-methoxyphenyl, 6-methoxy-3-methylphenyl, 5-chloro-6-methoxyphenyl, 2-chloro-5-methoxyphenyl, 2-methyl-4-methoxyphenyl or 3,4-dimethoxyphenyl. Still another preferred class of compounds include those wherein aryl represents 2-methylphenyl, 2,4-dimethylphenyl, 3,5-dimethylphenyl or 4-methylphenyl. An additional preferred class of compounds includes those wherein aryl represents 2,5-difluorophenyl, 2-fluorophenyl, 2,4-dichlorophenyl, 2-chlorophenyl and 3-chloro-4-fluorophenyl.

The anti-inflammatory activity of the thiourea compounds was determined in procedures analagous to the method of Winter et al. described in "Proceedings of the Society for Experimental Biology and Medicine", vol. 111, p. 544 (1962). In such operations, edema is induced by injection into the plantar surface of the right hind paw of a rat of carrageenin, prepared as a 1 percent suspension in sterile glass distilled water. The volume injected is 0.1 ml. The volume of the paw is measured immediately after injection with carrageenin and again 3 hours later. The difference in volume between the two measurements indicates the increase due to swelling caused by edematous fluid. Rat paw volume is measured by plethesmography. The percent decrease in milliliters displaced as compared to untreated controls is expressed as percent inhibition of edema.

One hour before injection with carrageenin the test animals are orally administered the test ingredient suspended (or dissolved) in 0.5% carboxymethylcellulose (1 ml/100 grams) and sufficient water to equal a total volume of 5 mls.

The following table shows the percentage of inhibition caused by the thiourea compounds of the formula:

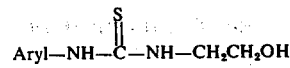

TABLE I

| | Test Compound Aryl | Oral Dose mg/kg | Inhibition of Edema, percent |
|---|---|---|---|
| 1.(a) | 2,4-dimethylphenyl | 7.5 | −48.9 |
| (b) | 2,4-dimethylphenyl | 15.0 | −75.5 |
| (c) | 2,4-dimethylphenyl | 30.0 | −79.8 |
| 2. | 4-methoxy-2-methylphenyl | 50.0 | −77.8 |
| 3. | 3,5-dimethylphenyl | 60.0 | −41.5 |
| 4. | 3,4-dimethoxyphenyl | 60.0 | −28.8 |
| 5. | 6-methoxy-3-methylphenyl | 60.0 | −38.0 |
| 6. | 2,5-difluorophenyl | 60.0 | −25.9 |
| 7. | 3-chloro-2-methoxyphenyl | 60.0 | −53.9 |
| 8. | 4-methylphenyl | 60.0 | −54.7 |

TABLE I-continued

| | Test Compound Aryl | Oral Dose mg/kg | Inhibition of Edema, percent |
|---|---|---|---|
| 9. | 2-methylphenyl | 60.0 | −55.8 |
| 10. | 2,4,6-trimethylphenyl | 60.0 | −76.9 |
| 11. | 2-fluorphenyl | 60.0 | −34.0 |
| 12. | 2,4-dichlorophenyl | 60.0 | −44.5 |
| 13. | 2-chlorophenyl | 60.0 | −40.5 |
| 14. | 2-chloro-5-methoxyphenyl | 60.0 | −44.1 |
| 15. | 3-chloro-4-fluorophenyl | 60.0 | −53.6 |
| 16. | 2,4-dimethylbenzyl | 60.0 | −41.1 |
| 17. | 3,4-dimethoxyphenyl | 60.0 | −28.8 |
| 18. | 2-methyl-4-methoxyphenyl | 60.0 | −38.0 |
| 19. | 4-chloro phenyl | 60.0 | −66.6 |
| 20. | *Phenylbutazone | 60.0 | −42.0 |

*A commercially available product.

The method of treating inflammation in accordance with this invention comprises administering internally to a mammal a compound as represented by Formula I, usually combined with a pharmaceutical excipient or carrier, in an amount sufficient to produce an anti-inflammatory effect. Preferably, the compounds are administered orally. Advantageously, equal doses will be administered from one to six times daily.

The dosage required to achieve anti-inflammatory activity in the animal will vary with various factors such as the species of animals, general health and tolerances of the animal, weight, sex and age of the animal, the nature and severity of the disease being treated and the like. Additionally, it is to be noted that the exact dosage of each individual compound employed in similar situations will vary. Generally, a total daily dosage would be in the range of from about 1.0 to about 150.0 milligrams or more per kilogram of body weight, usually from 5.0 to about 75.0 milligrams per kilogram of body weight.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

That which is claimed is:

1. A method of alleviating an inflammatory condition in a mammal which comprises administering to said mammal an anti-inflammatory effective amount of a compound of the formula:

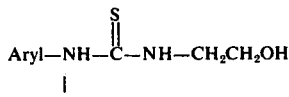

$$\text{Aryl}-\text{NH}-\overset{\overset{\text{S}}{\|}}{\text{C}}-\text{NH}-\text{CH}_2\text{CH}_2\text{OH}$$

wherein aryl represents 2,4-dimethylphenyl, 4-methylphenyl, 3,5-dimethylphenyl, 2-methylphenyl, 2,4,6-trimethylphenyl, 3,4-dimethylphenyl, 2,6-dimethylphenyl, 3-methylphenyl, 2,5-dimethylphenyl, 2,4-dimethylbenzyl, 3,4-dimethoxyphenyl, 4-methoxy-2-methylphenyl, 6-methoxy-3-methylphenyl, 2-fluorophenyl, 3-fluorophenyl, 2,6-difluorophenyl, 2,5-difluorophenyl, 4-chlorophenyl, 2,4-dichlorophenyl, 2-chlorophenyl, 2,4,6-trichlorophenyl, 3-chloro-2-methoxyphenyl, 5-chloro-6-methoxyphenyl, 2-chloro-5-methoxyphenyl and 3-chloro-4-fluorophenyl.

2. A method as in claim 1 wherein aryl represents 2,4-dimethylbenzyl, 3,5-dimethylphenyl, 4-methylphenyl or 2,4,6-trimethylphenyl.

3. A method as in claim 1 wherein aryl represents 3-chloro-2-methoxyphenyl, 6-methoxy-3-methylphenyl, 5-chloro-6-methoxypheyl, 2-chloro-5-methoxyphenyl, 2-methyl-4-methoxyphenyl or 3,4-dimethoxyphenyl.

4. A method as in claim 1 wherein aryl represents 2-methylphenyl, 2,4-dimethylphenyl, 3,5-dimethylphenyl or 4-methylphenyl.

5. A method as in claim 1 wherein aryl represents 2,5-difluorophenyl, 2-fluorophenyl, 2,4-dichlorophenyl, 2-chlorophenyl and 3-chloro-4-fluorophenyl.

6. A method as in claim 1 wherein said compound is 1-(2,4-dimethylphenyl)-3-(2-hydroxyethyl)thiourea.

7. A method as in claim 1 wherein said compounds is 1-(4-methoxy-2-methylphenyl)-3-(2-hydroxyethyl)thiourea.

8. A method as in claim 1 wherein said compound is 1-(3,5-dimethylphenyl)-3-(2-hydroxyethyl)thiourea.

9. A method as in claim 1 wherein said compound is 1-(3,4-dimethoxyphenyl)-3-(2-hydroxyethyl)thiourea.

10. A method as in claim 1 wherein said compound is 1-(6-methoxy-3-methylphenyl)-3-(2-hydroxyethyl)thiourea.

11. A method as in claim 1 wherein said compound is 1-(2,5-difluorophenyl)-3-(2-hydroxyethyl)thiourea.

12. A method as in claim 1 wherein said compound is 1-(3-chloro-2-methoxyphenyl)-3-(2-hydroxyethyl)thiourea.

13. A method as in claim 1 wherein said compound is 1-(4-methylphenyl)-3-(2-hydroxyethyl)-thiourea.

14. A method as in claim 1 wherein said compound is 1-(2-methylphenyl)-3-(2-hydroxyethyl)thiourea.

15. A method as in claim 1 wherein said compound is 1-(2,4,6-trimethylphenyl)-3-(2-hydroxyethyl)thiourea.

16. A method as in claim 1 wherein said compound is 1-(2-fluorophenyl)-3-(2-hydroxyethyl)thiourea.

17. A method as in claim 1 wherein said compound is 1-(2,4-dichlorophenyl)-3-(2-hydroxyethyl)thiourea.

18. A method as in claim 1 wherein said compound is 1-(2-chlorophenyl)-3-(2-hydroxyethyl)thiourea.

19. A method as in claim 1 wherein said compound is 1-(2-chloro-5-methoxyphenyl)-3-(2-hydroxyethyl)thiourea.

20. A method as in claim 1 wherein said compound is 1-(3-chloro-4-fluorophenyl)-3-(2-hydroxyethyl)thiourea.

21. A method as in claim 1 wherein said compound is 1-(2,4-dimethylbenzyl)-3-(2-hydroxyethyl)thiourea.

22. A method as in claim 1 wherein said compound is 1-(3,4-dimethoxyphenyl)-3-(2-hydroxyethyl)thiourea.

23. A method as in claim 1 wherein said compound is 1-(2-methyl-4-methoxyphenyl)-3-(2-hydroxyethyl)thiourea.

24. A method as in claim 1 wherein said compound is 1-(4-chlorophenyl)-3-(2-hydroxyethyl)thiourea.

25. A method as in claim 1 wherein said anti-inflammatory amount is a daily dose in the range of from about 1.0 to about 150.0 mg/kg of body weight of mammal.

26. A method as in claim 1 wherein said anti-inflammatory amount is a daily dose in the range of from about 5.0 to about 75.0 mg/kg of body weight of mammal.

* * * * *